(12) United States Patent
Thompson et al.

(10) Patent No.: US 6,206,894 B1
(45) Date of Patent: Mar. 27, 2001

(54) ELECTRICALLY POWERED NEEDLE HOLDER TO ASSIST IN SUTURING

(75) Inventors: Bennie Thompson, Cincinnati; Christopher A. Papa, Loveland; Jeffrey Swayze, Cincinnati, all of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/412,480

(22) Filed: Oct. 5, 1999

Related U.S. Application Data

(63) Continuation-in-part of application No. 09/012,783, filed on Jan. 23, 1998, which is a continuation-in-part of application No. 08/946,820, filed on Oct. 9, 1997, now Pat. No. 6,106,533.

(51) Int. Cl.$^7$ .................................................. A61B 17/062
(52) U.S. Cl. ........................................ 606/144; 606/147
(58) Field of Search ................................... 606/144, 148, 606/147

(56) References Cited

U.S. PATENT DOCUMENTS

| | | | |
|---|---|---|---|
| 2,601,564 | 6/1952 | Smith | 128/340 |
| 4,236,470 | 12/1980 | Stenson | 112/169 |
| 4,635,638 | 1/1987 | Weintraub | 128/340 |
| 4,899,746 | 2/1990 | Brunk | 606/144 |
| 5,100,421 | 3/1992 | Christoudias | 606/147 |
| 5,152,769 | 10/1992 | Baber | 606/145 |
| 5,171,257 | 12/1992 | Ferzli | 606/205 |
| 5,224,948 | 7/1993 | Abe | 606/147 |
| 5,261,917 | 11/1993 | Hasson | 606/139 |
| 5,300,082 | 4/1994 | Sharpe | 606/147 |
| 5,389,103 | 2/1995 | Melzer | 606/144 |
| 5,397,325 | 3/1995 | Della Badia | 606/144 |
| 5,431,670 | 7/1995 | Holmes | 606/147 |
| 5,454,823 | 10/1995 | Richardson | 606/148 |
| 5,545,148 | 8/1996 | Wurster | 604/223 |
| 5,571,090 | 11/1996 | Sherts | 606/144 |
| 5,582,617 | 12/1996 | Klieman | 606/170 |
| 5,735,862 | 4/1998 | Jennings | 606/147 |
| 5,746,753 | 5/1998 | Sullivan | 606/147 |
| 5,759,188 | 6/1998 | Yoon | 606/147 |
| 5,779,130 | 7/1999 | Alesi | 227/176 |
| 5,814,054 | 9/1998 | Kortenback | 606/139 |

FOREIGN PATENT DOCUMENTS

| | | | |
|---|---|---|---|
| 482 881 | 4/1992 | (EP) | A61B/17/04 |
| 337.579 | 12/1903 | (FR) | . |
| 2 260 704 | 4/1993 | (GB) | A61B/17/04 |
| WO 98/12372 | 3/1998 | (WO) | . |

Primary Examiner—Michael H. Thaler
(74) Attorney, Agent, or Firm—Dean Garner

(57) ABSTRACT

In accordance with the present invention there is provided a device for use with a needle with a suture attached to it. The device is used for suturing bodily tissue and comprises a handle, a right arm and a left arm extending distally from the handle. The distal end of the right arm has a right gripper attached to it for gripping and releasing the needle. The distal end of the left arm has a left gripper attached to it for gripping and releasing the needle. The device further comprises an electrically powered means for operating the left gripper and the right gripper. The left gripper and the right gripper exchange gripping of the needle. One of the left gripper and the right gripper moves near to the other to exchange gripping of the needle and moves apart from the other when not gripping the needle. The device further comprises a control unit for controlling the electrically powered means. In one embodiment, the electrically powered means comprises a drive assembly contained in the handle, and the drive assembly has an electrically powered motor.

6 Claims, 13 Drawing Sheets

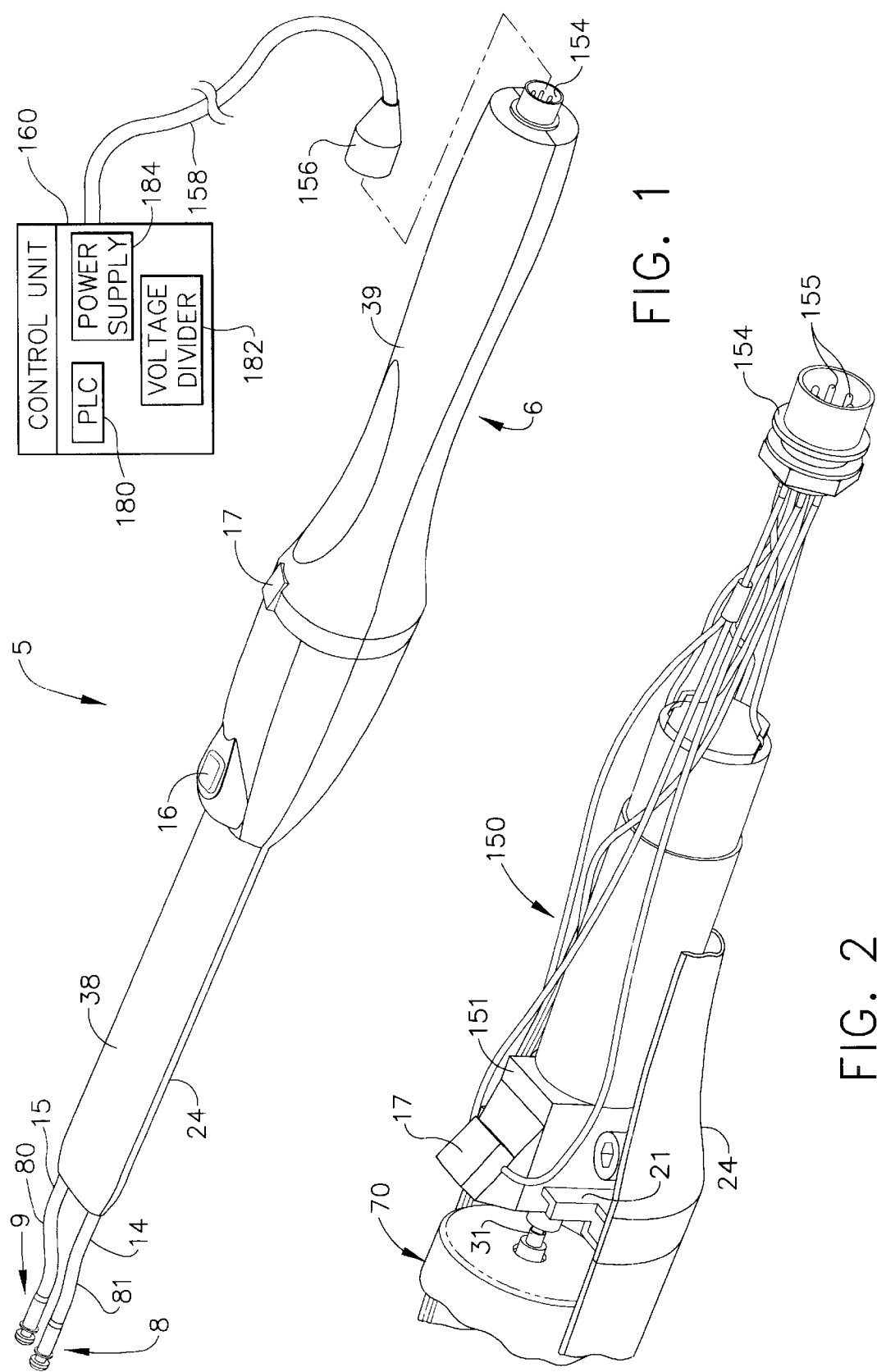

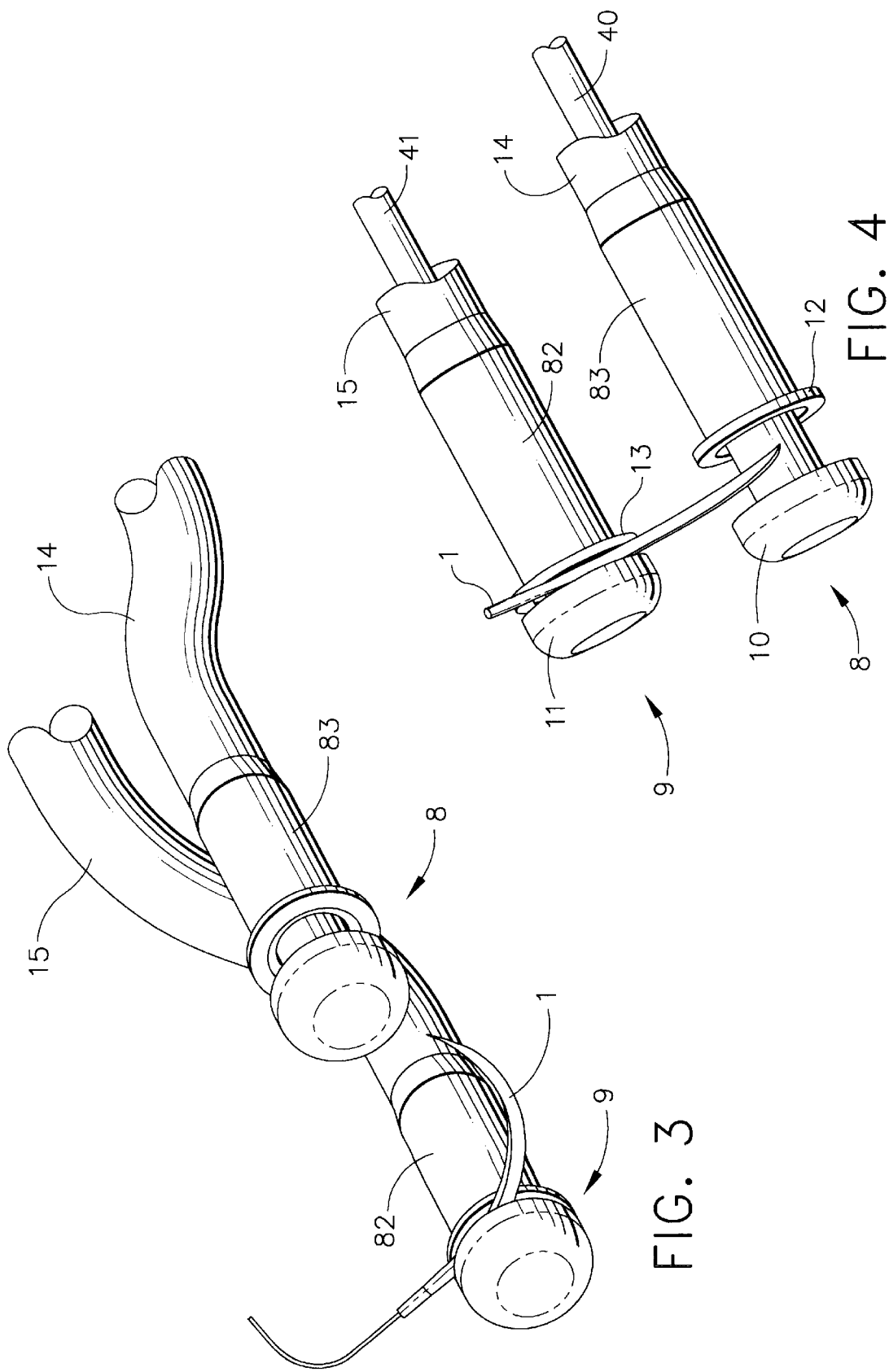

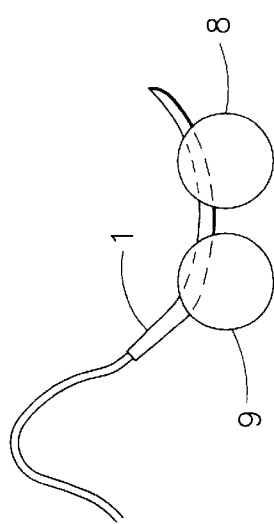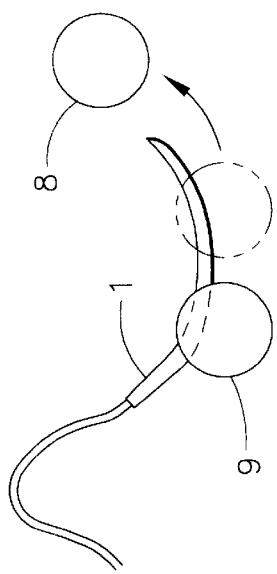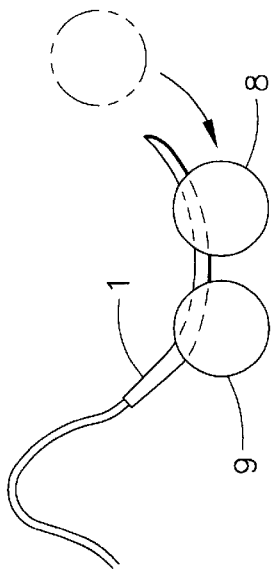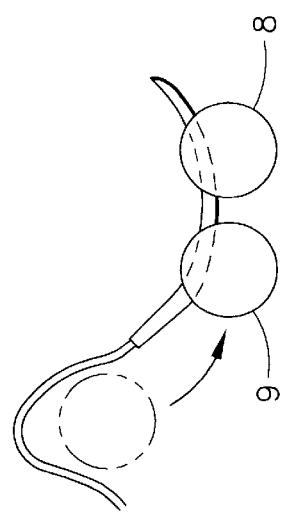

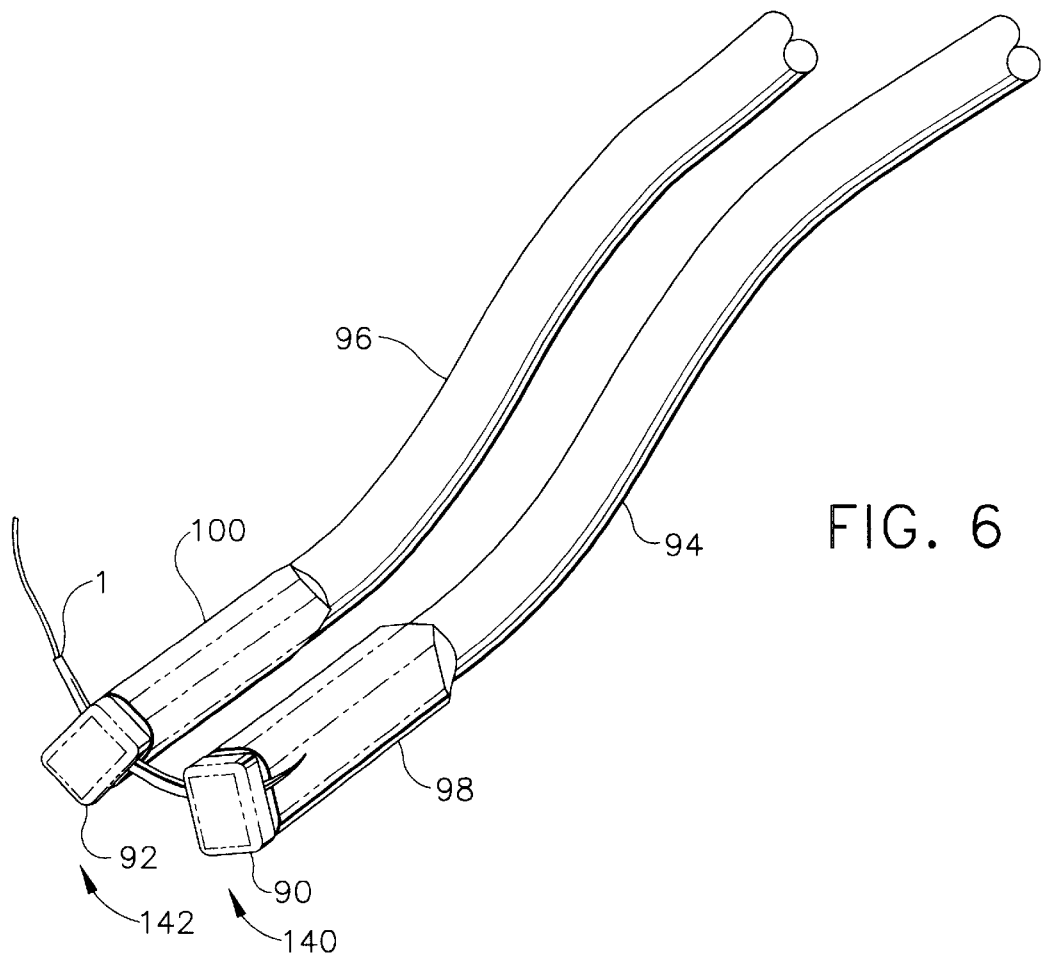
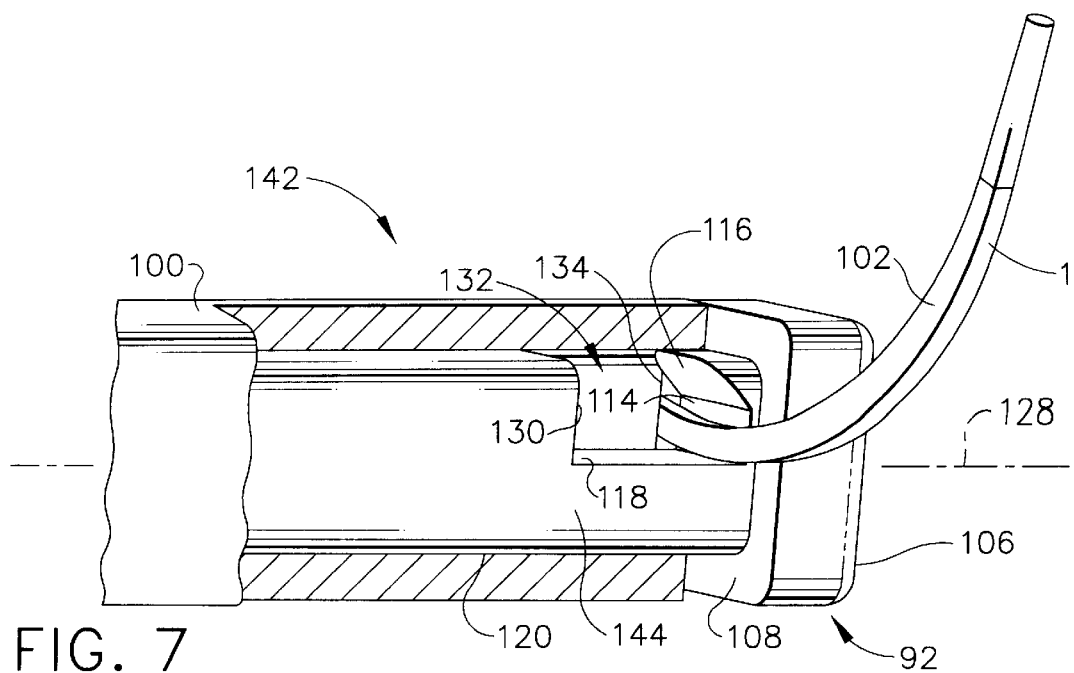

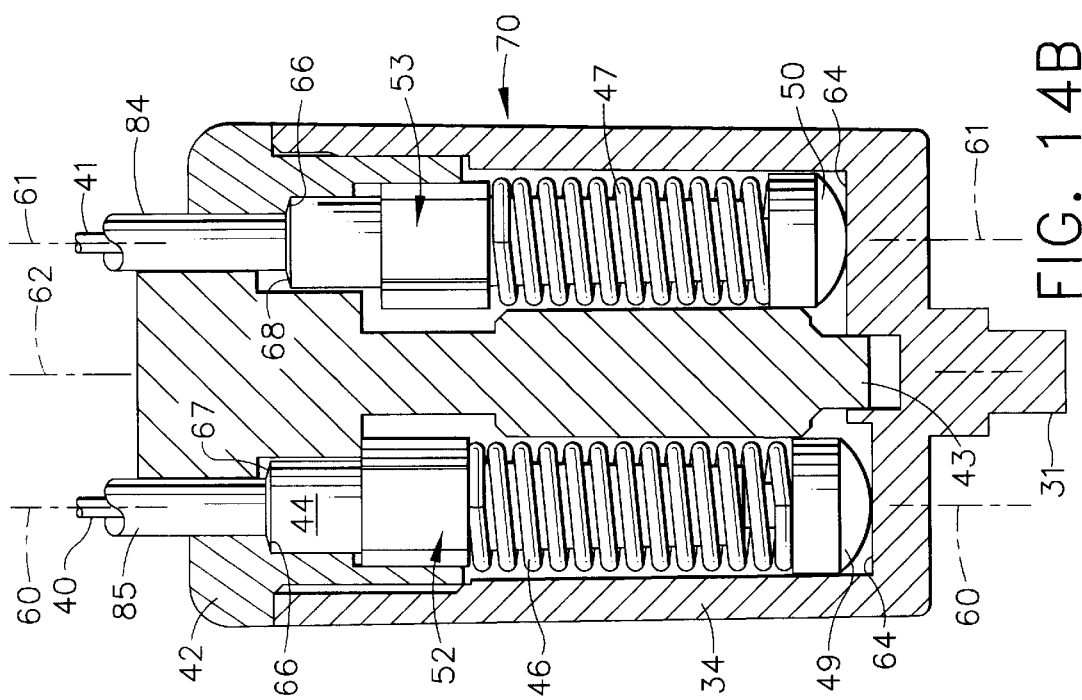
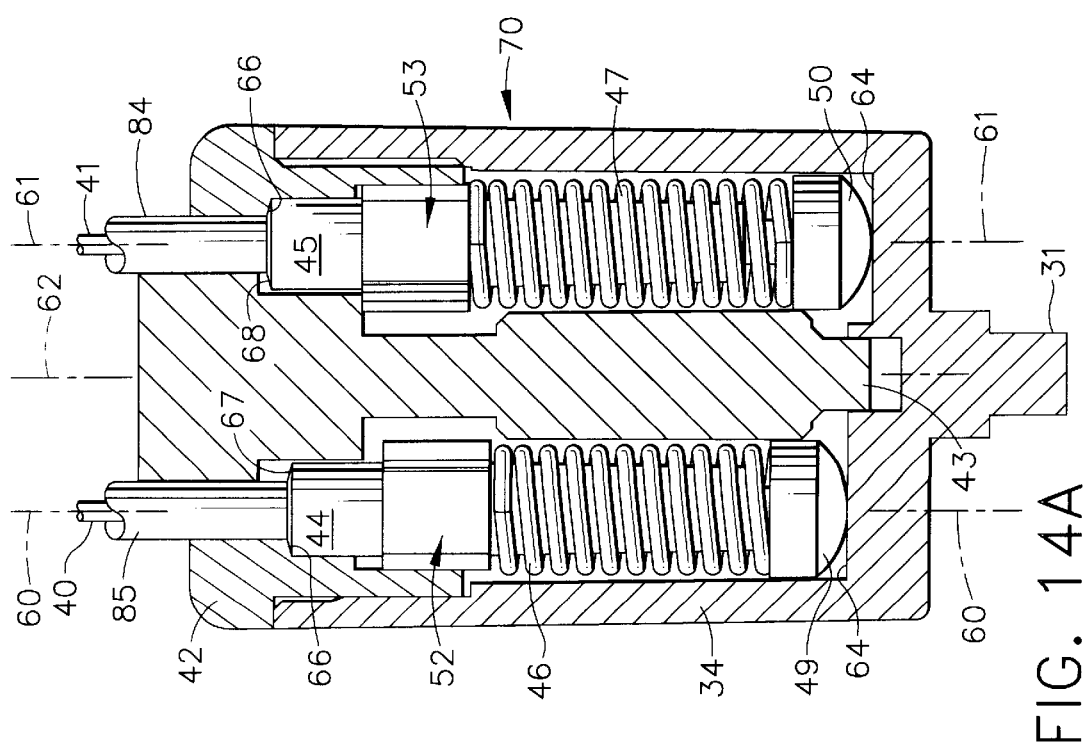

ELECTRICALLY POWERED NEEDLE HOLDER TO ASSIST IN SUTURING

The present invention is a continuation-in-part to U.S. patent application Ser. No. 09/012783 filed Jan. 23, 1998, which is a continuation-in-part to U.S. patent application Ser. No. 08/946820 filed Oct. 9, 1997, now U.S. Pat. No. 6,106,533 both titled "A Needle Holder to Assist in Suturing."

FIELD OF THE INVENTION

The present invention relates to the field of medicine and more particularly to surgery. More specifically, the present invention relates to surgical devices and methods for suturing bodily tissues both for open surgical procedures and for endoscopic surgical procedures. The present invention especially relates to surgical devices and methods for joining hollow organs, e.g. the anastomosis of the small or large intestines, and blood vessels, for joining them together in end-to-end, end-to-side, or side-to-side fashion.

BACKGROUND OF THE INVENTION

It is common surgical practice to use bypass grafts to help reestablish coronary artery circulation when a portion of the coronary artery is stenosed. Such a procedure is typically referred to as a coronary artery bypass graft (CABG) procedure. Typically the graft vessel used in bypassing a stenosed portion of the coronary artery is a segment of the patient's saphenous vein which is taken from the patient's leg. Other graft vessels such as the radial artery in the arm can also be used. In addition, it is common practice today for the surgeon to redirect one of the internal mammary arteries (IMA) in the chest to the stenosed portion of the left anterior descending (LAD) artery on the heart. The IMA is mobilized and then the free end is joined to the LAD, just distal to the blockage. For multiple bypass surgery, a combination of the redirection of the IMA and the grafting of vessels to the diseased coronary arteries is often used.

When a surgeon performs an anastomosis of the graft vessel to the coronary artery, it is important that the graft vessel be held steady and adjacent to the coronary artery, with a minimum of vascular trauma and a minimum of visual and surgical obstruction by instruments in the narrow operative field. The speed of performing such an anastomosis is extremely critical as well. Often the coronary artery is intentionally but temporarily occluded during the procedure, using any of a number of occlusion devices currently available, so that each anastomosis can be performed more easily. It is very important to perform the anastomosis and remove the occluding device in order to reconnect the supply of blood to the artery as soon as possible, thus minimizing trauma to the vessels and surrounding tissue.

Blood vessels are typically anastomosed end-to-end or end-to-side using any of a number of manual suturing techniques. For example, the surgeon may use a conventional needle holder in combination with a tissue grasper to suture two vessels together in the following manner. After an arteriotomy has been done on the coronary artery to create an opening to the lumen (inside) of the artery, the surgeon first passes the tip of a curved suturing needle having a suture attached to the blunt end through the graft vessel wall from the outside. Usually a knot or button is present at the trailing end of the suture to anchor the first stitch. Then the needle is passed through the coronary artery wall from inside the lumen. The needle is then passed again through the graft vessel wall from the outside. Next the surgeon grasps the needle near the tip and pulls the needle through the walls of the vessels with the suture following the path of the needle. The surgeon then pulls the suture through the vessel walls to form the first stitch. The surgeon then penetrates the tip of the needle through the inside of the coronary artery wall again, at a location spaced apart from the first stitch. The surgeon again passes the needle through the coronary artery wall and into the outside of the graft vessel wall. The surgeon grasps the needle near the tip and pulls the suture through the vessel walls to form the second stitch. This process is repeated with the surgeon carefully tensioning the suture after each stitch to draw the vessel walls together, thereby creating a running stitch around the vessel and composed of a plurality of individual suture loops. When the graft vessel wall has been thus sutured around its entire perimeter to the coronary artery wall, the two strands of suture are tied together and trimmed to complete the anastomosis. As is evident by the foregoing description, manual suturing techniques are usually tedious and time-consuming, generally requiring several minutes to complete for each anastomosis, even for a highly skilled surgeon.

In the surgical art, the use of time-tested surgical techniques is generally very important to surgeons. When suturing, a traditional technique for using a needle holder to place a curved needle into tissue is often referred to as supination, or the turning of the palm inwards. This simply means that once the tip of the curved needle is carefully placed into the tissue, the hand holding the needle holder is rotated so that the curved needle is driven through the tissue up to the point where the needle holder is clamped onto the needle. The needle holder is released from the needle, and clamped again on the portion of the needle extending from the opposite side of the tissue penetrated. Then supination is again used to pull the remainder of the needle through the tissue. Using this technique, the needle follows an arcuate path in a direction transverse to the longitudinal axis of the needle holder. It is very advantageous, therefore, that a device for facilitating the suturing of bodily tissues also allows the surgeon to use the supination technique.

There are a number of examples of devices designed to facilitate the suturing of tissue during surgical procedures. Such examples are described in U.S. Pat. No. 5,437,681 issued to Meade, et al, on Aug. 1, 1995 and U.S. Pat. No. 5,540,705, also issued to Meade, et al, on Jul. 30, 1996. Those devices drive a needle through the tissues being joined together. A disadvantage of the Meade devices, however, is the removal of the surgeon's tactile sensation as the needle is penetrated into the tissue. This may affect the surgeon's perception of control of the suturing technique. Furthermore, the Meade devices do not permit the surgeon to use hand supination when penetrating the needle into tissue. What is needed is an automated suturing device that allows the surgeon to use hand supination and to maintain tactile sensation of the needle as it is penetrating the tissue.

Several investigators have incorporated electrically powered means into suturing devices in order to automate the suturing of bodily tissues. Some of these devices are power-driven, needle-gripping tools such as described by Weintraub, et al, in U.S. Pat. No. 4,635,638 issued on Jan. 13, 1987. In U.S. Pat. No. 5,735,862 issued on Apr. 7, 1998 to Jennings, et al, a pair of electric solenoid driven gripping jaws is constructed into a pair of arms pivotally attached to each other. The jaws are automatically and alternatingly actuated to open and close when they are pivoted into proximity with each other, such that a hand-off of the needle can occur. For the Jennings device the surgeon maintains tactile sensation of the needle passing through tissue, but visibility of the tissue being sutured is not as good as with conventional manual suturing techniques. Also, because the arms are constructed to pivot with respect to each other in a plane, it would be difficult for the surgeon to use hand supination to place the needle into tissue. Other devices incorporate powered means for passing a specially designed surgical needle through tissue and have the disadvantage described earlier, that is, removal of tactile sensation and control from the surgeon. Examples of such devices are described in U.S. Pat. No. 5,545,148 to Wurster, issued on Aug. 13, 1996, and to Brunk in U.S. Pat. No. 4,899,746, issued on Feb. 13, 1990.

In the related parent patent applications, Ser. No. 08/946820 and 09/012783, shortcomings of the prior art are overcome. Embodiments of a suturing device (also referred to as a needle holder) are described which reduce the time to suture tissues. The embodiments also maintain surgeon control by permitting tactile sensation for when the needle is penetrating into tissue, and allowing the surgeon to use the hand supination suturing technique. In addition, visibility of the tissues being sutured is not obstructed by the suturing device. Despite these advantages, an opportunity to improve the device may be realized by reducing the manual force and movement necessary to actuate a trigger of the device. This would aid the surgeon in suturing especially small and delicate tissues such as blood vessels primarily because it would be easier to keep the distal end of the device steady as the needle is passed through the tissue.

The present invention is an improvement of the suturing device embodiments described in the related applications, 08/946820 and 09/012783, in that the advantageous features are retained in a novel combination with an electrically powered means, thus replacing the trigger with a small control button. This enables the surgeon to suture especially delicate bodily tissues easily and quickly with a single instrument. It is especially useful for creating a vascular anastomosis such as for a CABG procedure.

SUMMARY OF THE INVENTION

In accordance with the present invention there is provided a device for use with a needle with a suture attached to it. The device is used for suturing bodily tissue and comprises a handle, and a right arm and a left arm extending distally from the handle. The distal end of the right arm has a right gripper attached to it for gripping and releasing the needle. The distal end of the left arm has a left gripper attached to it for gripping and releasing the needle. The device further comprises an electrically powered means for operating the left gripper and the right gripper. The left gripper and the right gripper exchange gripping of the needle. One of the left gripper and the right gripper moves near to the other to exchange gripping of the needle and moves apart from the other when not gripping the needle. The device further comprises a control unit for controlling the electrically powered means. In one embodiment, the electrically powered means comprises a drive assembly contained in the handle, and the drive assembly has an electrically powered motor. The present invention does not require high actuation force or movement by the surgeon's hand in order to operate it, and therefore the device can be held very steady while performing especially delicate suturing procedures.

The control unit of the device may be detachably connected to the electrically powered means. This allows the handle, the right arm, and the left arm to be either disposable or more easily cleaned/sterilized for multi-patient use. The device is provided with a switch on the handle so that the surgeon may conveniently actuate the electrically powered means.

In one embodiment of the present invention, the control unit comprises a programmable logic controller for controlling the electrical power for the electrically powered means. In another embodiment, the control unit comprises a load sensing circuit for controlling the electrical power for the electrically powered means.

The right arm of the device has a first offset bend proximal to said right gripper. The left arm has a second offset bend proximal to the left gripper. Rotation of the right arm about the longitudinal axis of the right arm causes the right gripper to move laterally along a first arcuate path. Rotation of the left arm about the longitudinal axis of the left arm causes the left gripper to move laterally along a second arcuate path. The first and second arcuate paths are substantially coplanar so that the needle may be passed from one of the first and second grippers to the other. The present invention permits the surgeon to use hand supination and to maintain tactile sensation of the needle penetration resistance while placing the needle into tissue.

The right gripper has a first and a second right opposing member. Each of the first and the second right opposing members moves towards the other to grip the needle, and moves away from the other to release the needle. The left gripper has a first and a second left opposing member. Each of the first and the second left opposing members moves towards the other to grip the needle, and moves away from the other to release the needle. This bi-directional opening and closing of the left and right grippers helps the instrument to reliably pass the needle from one gripper to the other.

BRIEF DESCRIPTION OF DRAWINGS

The foregoing and other aspects of the present invention will best be appreciated with reference to the detailed description of the invention in conjunction with the accompanying drawings, wherein:

FIG. 1 is an isometric view of an electrically powered needle holder and a generic view of a control unit;

FIG. 2 is an enlarged, partial view of the needle holder illustrated in FIG. 1, with a portion of a handle cover removed to reveal a drive assembly;

FIG. 3 is a front isometric view of the distal end of the needle holder illustrated in FIG. 1, showing a left gripper in an open position and, a right gripper holding a surgical needle, and the left gripper moved apart from the right gripper;

FIG. 4 is a top isometric view of the distal end of the needle holder illustrated in FIG. 1, showing the left gripper in the open position and the right gripper holding the surgical needle, and the left gripper moved near the right gripper;

FIG. 5A is an end view of the distal end of the needle holder illustrated in FIG. 1, showing the left and right grippers relatively near each other and gripping the surgical needle;

FIG. 5B is an end view of the distal end of the needle holder illustrated in FIG. 1, showing the left gripper moved laterally apart from the right gripper which is holding the surgical needle;

FIG. 5C is an end view of the distal end of the needle holder illustrated in FIG. 1, showing the left gripper moved laterally near the right gripper which is holding the surgical needle;

FIG. 5D is an end view of the distal end of the needle holder illustrated in FIG. 1, showing the right gripper moved laterally apart from the left gripper which is holding the surgical needle;

FIG. 5E is an end view of the distal end of the needle holder illustrated in FIG. 1, showing the right gripper moved laterally near the left gripper which is holding the surgical needle;

FIG. 6 is an isometric view of the distal end of an alternate embodiment of the left and right grippers of the needle holder, showing the left and right grippers holding a surgical needle and moved laterally near to each other;

FIG. 7 is a front isometric view of the distal end of the right gripper illustrated in FIG. 6, showing a portion of the right gripper removed to reveal the surgical needle being held between a right plunger and a right opposing member;

FIG. 14A is a top, sectional view of the barrel assembly illustrated in FIG. 13A;

FIG. 14B is a top, sectional view of the barrel assembly illustrated in FIG. 13B;

Figure 8:
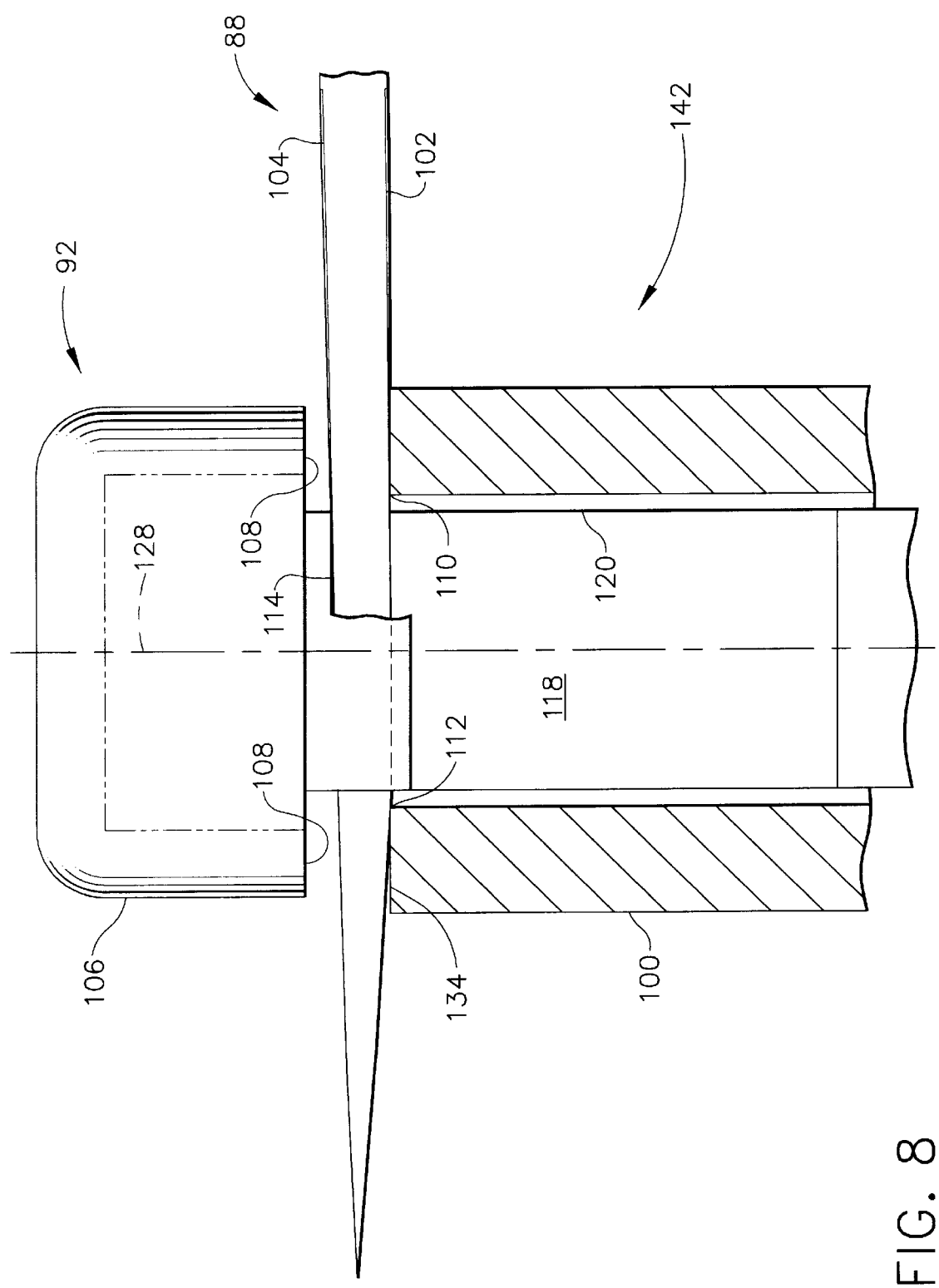
FIG. 8 is a top view of the right gripper illustrated in FIGS. 6 and 7, with a portion of the right gripper removed to reveal the surgical needle being held between the right plunger and the right opposing member.

The drawings are not necessarily to scale.

DETAILED DESCRIPTION OF THE INVENTION

The suturing device of the present invention can be used to suture any type of anatomical tissue that may also be sutured using the traditional surgical methods described earlier. The device described herein is for use through any sufficiently sized incision into the body, such as a mini-thoracotomy (incision between the ribs of the patient's chest), but may also be used on external portions of the body such as for plastic surgery. It should also be clear to one of ordinary skill in the art that the present invention can be configured and provided with sealing means so as to make it possible to use through an endoscopic port. The device described herein is shown being used with a surgical needle having a particular radius of curvature. It may also be used with needles having other curvature radii or of many other shapes and sizes, including skishaped and straight needles, depending on the surgeon's preference for the surgical procedure being performed.

Referring now to the figures wherein like numerals indicate the same elements throughout the views, there is shown in FIG. 1 a needle holder 5 in accordance with the present invention. Needle holder 5 includes a handle 6 having a button 16 and a motor actuating switch 17 (hereinafter referred to simply as a switch 17) whose functions will be explained in detail below. Handle 6 is ergonomically shaped so that a surgeon may comfortably grip it and actuate button 16 and switch 17 with the same hand. One-handed manipulation of needle holder 5 is advantageous because it frees the surgeon's other hand for holding another instrument during the surgical procedure. Extending distally from handle 6 is a left arm 14 and a right arm 15, each of which are preferably constructed from round tubular stainless steel, although substantial longitudinal portions of them may have other cross-sectional shapes such as rectangular or C-shaped. Left arm 14 has a left offset bend section 81. Right arm 15 has a right offset bend section 81. On left arm 14 is a left gripper 8. Similarly, on right arm 15 is a right gripper 9. The longitudinal axis of left gripper 8 is approximately parallel to the longitudinal axis of right gripper 9. The longitudinal axis of left arm 14 is approximately parallel to the longitudinal axis of right arm 15. Left gripper 8 and right gripper 9 are designed to grip alternatingly a surgical needle 1, as needle 1 passes from right arm 15 to left arm 14 and back again. The proximal portions of left arm 14 and right arm 15 may be exposed, but are preferably covered partially by an arm cover top 38 and cover bottom 24 as depicted in FIG. 1. The length of left arm 14 and right arm 15 may vary considerably without resulting in a change of the function or usage of the device.

The needle holder 5 is operationally connected to a control unit 160 depicted generically in FIG. 1. Control unit 160 has a control cord 158 of suitable length to allow the surgeon to position control unit 160 a few feet away from the surgical patient. A cable socket 156 attached to the distal end of control cord 158 may be connected to a panel plug 154 of the needle holder 5. Having control cord 158 detachable from needle holder 5 is preferred so that needle holder 5 may be discarded after use on a single patient while control unit 160 is reused. Needle holder 5 may also be constructed, however, to be multiple patients reusable.

Now referring to FIG. 2, a portion of cover bottom 24 and all of handle top 39 are removed to reveal a drive assembly 150 having a switch frame 151 which is mounted in a cradle 21 of the inside of cover bottom 24. When switch 17 is depressed, drive assembly 150 is actuated, imparting either a clockwise (CW) or counterclockwise (CCW) rotation to a barrel assembly 70 via a coupling 31, depending on when in the operational sequence switch 17 is depressed. As will be described later, the rotational direction of the barrel assembly 70 controls which of left gripper 8 or right gripper 9 is closing, and which is opening.

FIG. 3 shows right gripper 9 holding needle 1 while left gripper 8 is open and moved laterally apart from right gripper 9. FIG. 4 shows right gripper 9 still holding needle 1, but left gripper 8 is now moved laterally near right gripper 9 in order to receive needle 1. Right gripper 9 comprises a right gripper head 11 and a right arm flange 13 on a distal end 82 of right arm 15. Left gripper 8 comprises a left gripper head 10 and a left arm flange 12 on a distal end 83 of left arm 14. The sides of needle 1 are preferably flat to help prevent needle 1 from rotating while held between either left gripper head 10 and left arm flange 12, or between right gripper head 11 and right arm flange 13. A left cable 40 is slidably assembled inside of left arm 14 and attached to left gripper head 10 for opening and closing left gripper 8. Similarly, a right cable 41 is slidably assembled inside of right arm 15 and attached to right gripper head 11 for opening and closing right gripper 9.

A simplified description of the sequence of operation of the present invention is depicted in FIGS. 5A–5E. In FIG. 5A needle 1 is shown held by left gripper 8 and right gripper 9. When switch 17 is pressed and held, left arm 14 rotates CW so that left gripper 8 releases needle 1 and swings laterally away from right gripper 9 and stops at the position shown in FIG. 5B. The arc length of this swing motion is the same for each full actuation, where a full actuation occurs when switch 17 is depressed and held and either left gripper 8 or right gripper 9 moves to a new position and comes to a stop automatically. Switch 17 must then be released and then depressed again to continue in the operational sequence. It is possible to construct the present invention so that this arc length can be significantly more or less than what is shown in FIG. 5B. Needle 1 can now be manually placed through the tissue to be sutured by the surgeon. As noted earlier, the surgeon may use a hand supination technique. After placing needle 1 into the tissue, switch 17 is next depressed and held so that left gripper 8 moves laterally near right gripper 9 and can grip needle 1 again as shown in FIG. 5C, while right gripper 9 is still holding needle 1. When switch 17 is released and then pressed again, right gripper 9 releases needle 1 and swings laterally away from left gripper 8 to the position shown in FIG. 5D. In this position the surgeon manually moves needle 1 away from the tissue, again using wrist supination, and pulls the trailing suture through the tissue. Once this is done, switch 17 is again depressed and held so that right gripper 9 grips needle 1 again as shown in FIG. 5E. Pressing switch 17 repeats the foregoing operational sequence.

In the foregoing description for FIGS. 5A–E, needle 1 is described as being passed from the right gripper 9 to the left gripper 8 and them back to the right gripper 9. It is also possible, however, for the point of needle 1 to be directed in the opposite lateral direction. In that case, needle 1 would be passed from the left gripper 8 to the right gripper 9 and then back to the left gripper 8. It should be noted also that the traditional surgical technique for pitching and catching a needle has been maintained in the present invention. A twisting motion of the surgeon's hand is used to penetrate the tissue with needle 1 as well as to pull needle 1 and trailing suture out of the tissue. This is advantageous in that the surgeon still controls the precise placement and manipulation of needle 1, yet is able to do so with one instrument rather than with two as when using traditional suturing techniques.

An alternate embodiment of the distal portion of the present invention is illustrated in FIGS. 6, 7, and 8. The remainder of the needle holder 5 is the same as the previous embodiment first shown in FIG. 1. In FIG. 6, needle 1 is shown being held simultaneously by a left gripper 140 and a right gripper 142. Right gripper 142 includes a right plunger 92 (which may also be referred to as a second right opposing member) and a right opposing member 100 (which may also be referred to as a first right opposing member).

Right opposing member 100 is the distal portion of a tubular, right arm 96 and is formed into a rectangular cylinder. Right plunger 92 fits slideably into an aperture 144 (see FIG. 7) of right opposing member 100, and aperture 144 is surrounded by a perimeter wall 134 (see FIG. 7). The features of the left gripper 140 mirror those of the right gripper 142. The left gripper 140 comprises a left plunger 90 (also referred to as a first left opposing member) and a left opposing member 98 (also referred to as a second left opposing member), attached to the distal end of a left arm 94. Needle 1 has flattened sides to facilitate clamping and alignment in left gripper 140 and right gripper 142. The embodiment shown in FIGS. 6 and 7, however, may be used with round wire needles also.

In FIG. 7, needle 1 is shown being held by right gripper 142, which has been partially cut away for clarity. Plunger 92 includes a shank 120 extending slideably into right opposing member 100 and a hooking recess 132 defined by a shank wall 130, a shelf 118, a clamping member 114, and an inclined surface 116. A flange 106 is on the distal end of shank 120 and has an alignment surface 108. Clamping member 114 is slightly proximal and approximately parallel to alignment surface 108. Needle 1 is held between clamping member 114 and a perimeter wall 134 of right opposing member 100. As can be seen in this FIG. 7, needle 1 is trapped within the hooking recess 132 and is held upright so that the longitudinal axis of opposing member 100 is approximately normal to the plane containing needle 1. Needle 1 may be placed into or out of hooking recess 132 when gripper flange 106 is separated sufficiently from perimeter wall 134, during the sequence of operation of the device. Needle 1 is held in the proper orientation for suturing through tissue by the steps already described for FIGS. 5A–E. The reason needle 1 self-orients into this configuration and why this alternate embodiment also allows for a more secure grip on needle 1 than in the previous embodiment of FIG. 1 is described next.

FIG. 8 is an enlarged, sectional top view of a portion of right gripper 142 of the alternate embodiment first shown in FIGS. 6 and 7. Right opposing member 100 and right plunger 92 are shown holding the tapered portion of needle 1. The curved needle 88 includes a first and a second flattened surface, 102 and 104, respectively. First flattened surface 102 is held against perimeter wall 134 at first and second locations, 110 and 112, respectively, which are spaced laterally apart. Clamping member 114 of plunger 92 clamps against second flattened surface 104 of needle 1, and on a portion of the curved needle laterally between the first and second locations, 110 and 112. In this arrangement, needle 1 essentially is a simply loaded beam that bends slightly when under load. How much needle 1 bends depends on the force applied by the plunger 92, but this force is well below that required for the needle material to yield, so that release of needle 1 by the plunger 92 allows needle 1 to straighten to its original shape. By clamping onto needle 1 in this manner, the resistance of the needle to slip laterally during suturing into tissue is significantly increased as compared to the embodiment of FIG. 1. It is also possible to construct the present invention as embodied in FIGS. 6–8 so that right plunger 92 is stationary and right opposing member 100 moves distally, thus gripping needle 1 therebetween. The foregoing description of how needle 1 is held in right gripper 142 also applies to how it is held in left gripper 140.

Figure 9:
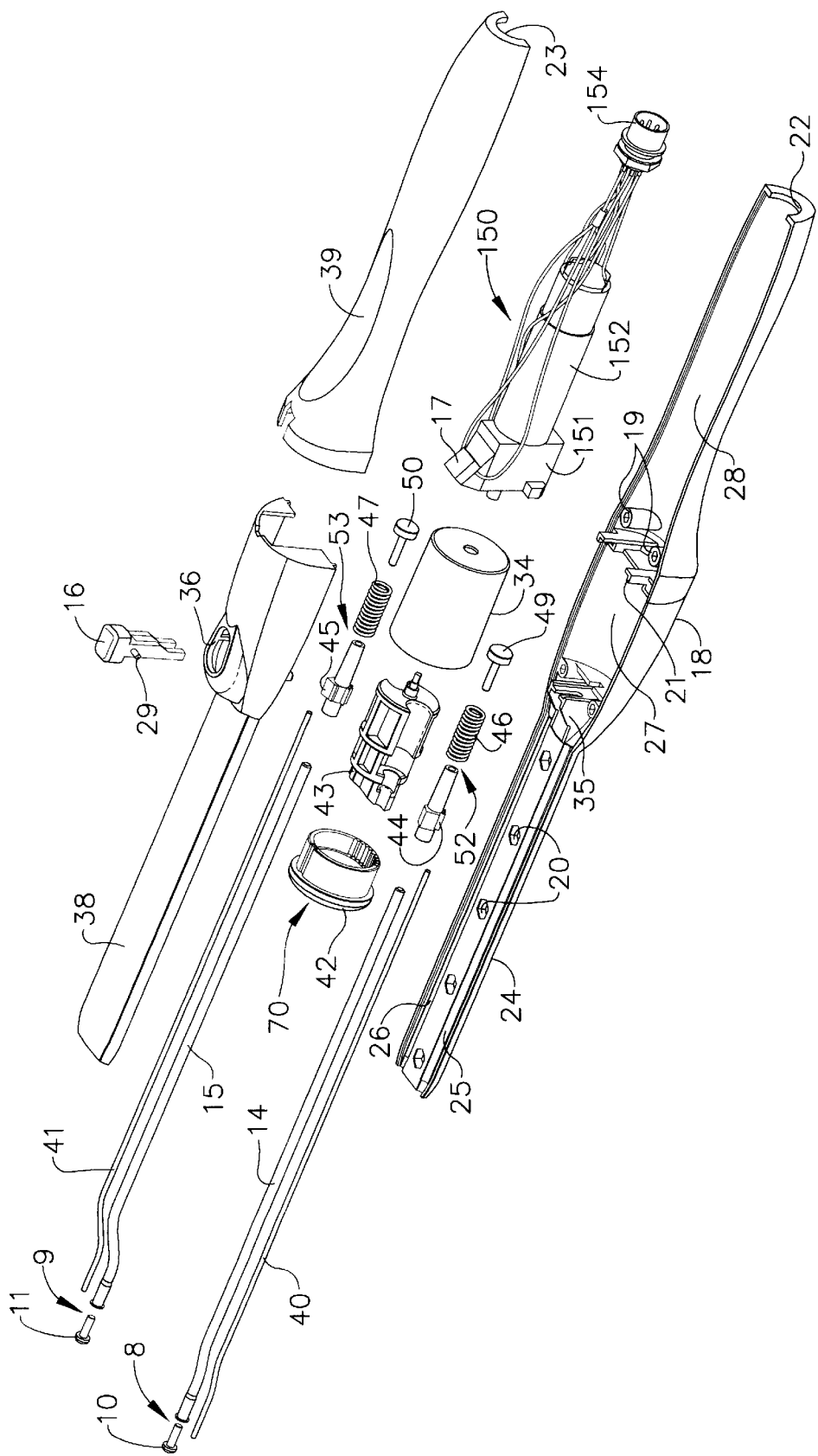
FIG. 9 is an exploded isometric view of the needle holder illustrated in FIG. 1.

FIG. 9 is an exploded isometric view of the embodiment of needle holder 5 of the present invention first shown in FIG. 1. Hollow left arm 14 slideably contains left cable 40 which is attached on its distal end to left gripper 10, thus assembling as left gripper 8. Hollow right arm 15 slideably contains right cable 41, which is attached on its distal end to right gripper 11, thus assembling as right gripper 9. Right cable 41 and left cable 40 are preferably made of braided stainless steel wires. Left gripper head 10 and right gripper head 11 are preferably made of stainless steel. Barrel assembly 70 comprises a left pinion assembly 52, a right pinion assembly 53, a yoke 43, a cam lid 42, and a barrel cover 34. Left pinion assembly includes a plastic injection molded left pinion 44 having a lumen therethrough, a left pinion spring 46, and a stainless steel, left cam head 49. Right pinion assembly 53 includes a plastic injection molded right pinion 45 having a lumen therethrough, a right pinion spring 47, and a stainless steel right cam head 50. The proximal end of left arm 14 attaches fixably to the distal end of left pinion 44 so that rotation of left pinion 44 about its longitudinal axis causes left arm 14 to rotate, thus resulting in the lateral swinging of left gripper 8, as described for FIGS. 5B and 5C. Cable 40 extends proximally through the lumen of left pinion 44 and attaches fixably to left cam head 49. Left pinion spring 46 is assembled between left pinion 44 and left cam head 49 in a partially compressed position so that left cam head 49 is normally forced in the proximal direction, thus causing left gripper head 10 to be in a closed position. Right pinion assembly 53 is assembled with right arm 15 and right gripper 9 in identical fashion. Rotation of right pinion 45 therefore causes rotation of right arm 15 so that right gripper 9 swings laterally as shown in FIGS. 5D and 5E. Left pinion assembly 42 and right pinion assembly 53 are assembled with yoke 43 between them into barrel 34. Cam lid 42 is a flanged, plastic injection molded cylinder which is pressed into barrel 34 to retain yoke 43, right pinion assembly 53, and left pinion assembly 52 in an operational engagement which will be described in detail for FIGS. 12–16. Barrel assembly 70 is rotatably retained in a center portion 18 of bottom cover 24. A mount 35 provides a vertical sliding surface for the distal side of button 16. The proximal side of button 16 slides against the distal end of yoke 43, which will be described in greater detail for FIGS. 15 and 16. Button 16 is plastic injection molded and is assembled into arm top cover 38 from underneath so that it projects through hole 36. A pair of nubs 29, one on each side of button 16, retains button 16 in arm top cover 38. A central cavity surface 27 provides a smooth bearing surface for the rotation of barrel assembly 70.

Still referring to FIG. 9, needle holder 5 further comprises drive assembly 150 having switch 17, switch frame 151, male connector half 154, and a motor 152. Drive assembly 150 is assembled inside a proximal cavity 28 of bottom cover 18, so that male connector half 154 is retained on lower recess 22. Needle holder 5 further comprises arm cover top 38, handle top 39 having an upper recess 23 for assembly over male connector half 154, and button 16. Arm cover top 38 and handle top 39 have a plurality of integrally molded gripper pins (not visible) for attachment to bottom cover 24 at fastening bosses 19 in a manner that is well-known in the art. Similarly, arm cover top 38 has a plurality of integrally molded gripper pins (not visible) for attachment to a like plurality of fastening holes 20 formed in bottom cover 24. Bottom cover 24, arm cover top 38, and handle top 39 are preferably injection molded from a rigid plastic such as polycarbonate.

Figure 10:
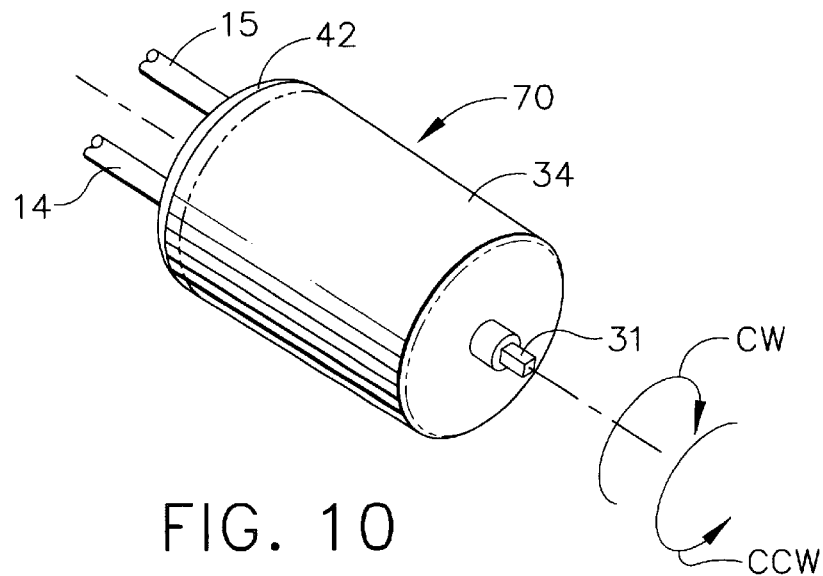
FIG. 10 is an isometric view of a barrel assembly also shown in FIG. 9.

FIG. 10 is an isometric view of barrel assembly 70 assembled to left arm 14 and right arm 15. A drive post 31 extends from the center of the proximal end of barrel assembly 70 for operational engagement with drive assembly 150 shown in FIG. 9. Rotation of barrel assembly 70 has two concurrently occurring functions with regard to the distal working end of needle holder 5. Rotation causes either left arm 14 or right arm 15 to rotate about their respective longitudinal axis, resulting in either the left gripper 8 or the right gripper 9 to swing apart or near to the other. It also causes either left gripper 8 or right gripper 9 to open or close, to allow the passing of needle 1 between them.

Figure 11:
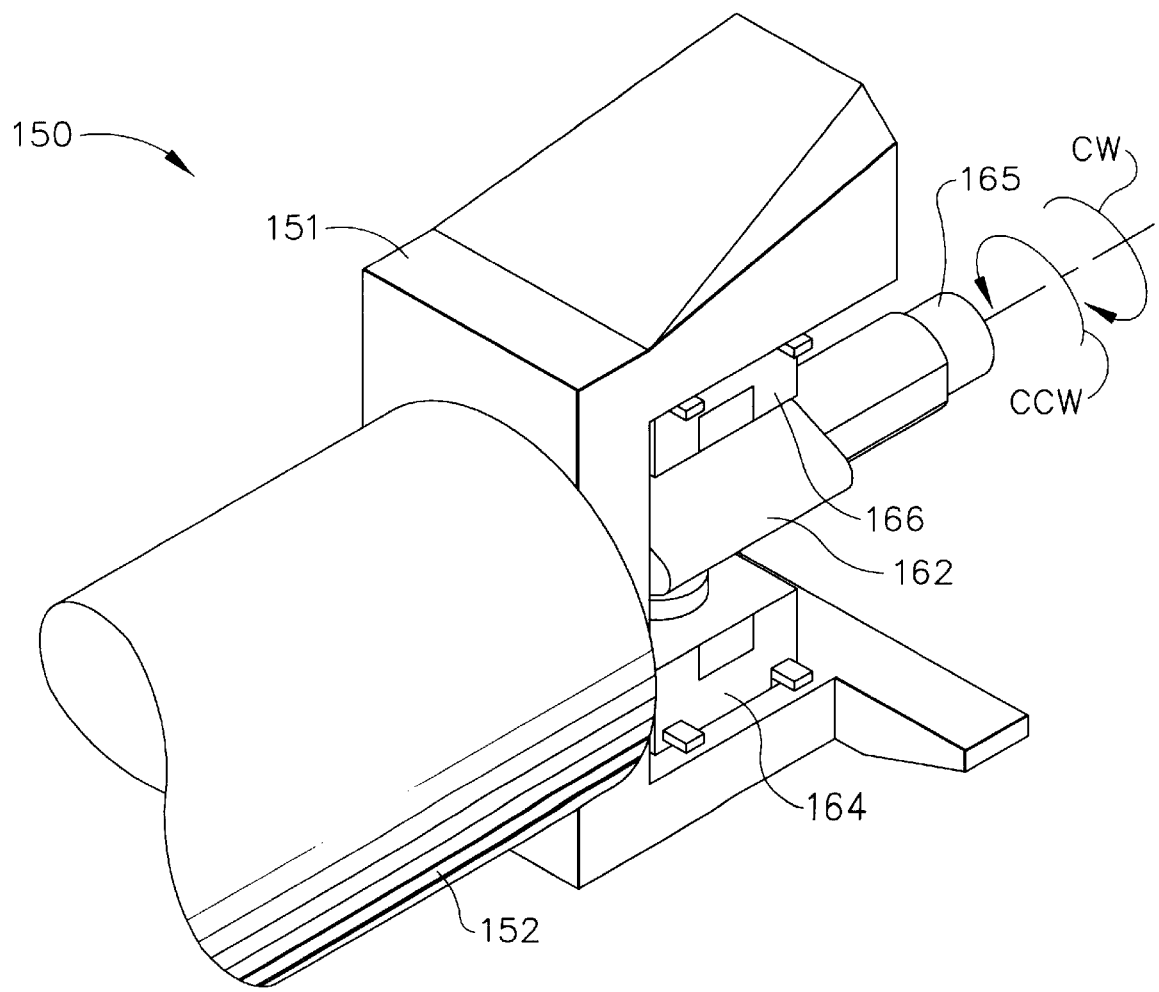
FIG. 11 is an isometric view of the drive assembly (without the electrical wires) also shown in FIG. 9.

FIG. 11 is an enlarged, isometric view of the distal portion of drive assembly 150 minus the wires and switch 17. A drive coupling 165 is provided for operationally engaging drive post 31 of barrel assembly 70 (see FIG. 10). Drive coupling 165 is attached to the armature shaft of motor 152 and includes a switching cam 166. Rotation of drive coupling 165 in a clockwise direction (when looking in the proximal to distal direction) causes switching cam 166 to rotate also in a clockwise direction to actuate a right limit switch 164 mounted in frame 151. Rotation of drive coupling 165 in a counterclockwise direction causes switching cam 166 to rotate in a counterclockwise direction to actuate a left limit switch 162 mounted in frame 151.

Figure 12:
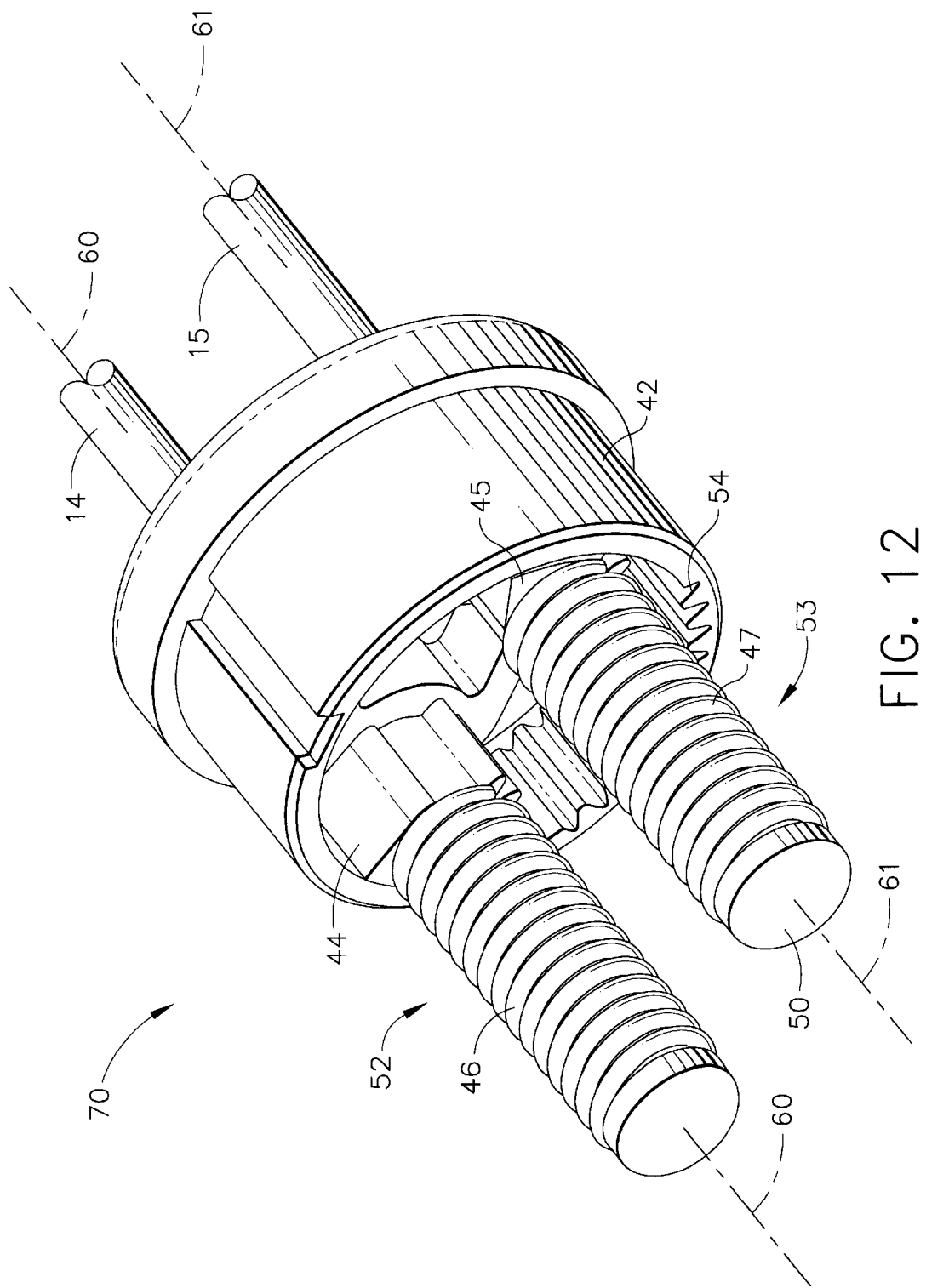
FIG. 12 is an isometric view of a portion of the barrel assembly illustrated in FIG. 10, revealing a left and a right pinion in engagement with a plurality of cam lid gear teeth.

FIG. 12 is an isometric view of barrel assembly 70 (see FIGS. 9 and 10), with barrel cover 34 and yoke 43 removed in order to reveal the operational engagement of left pinion assembly 52 and right pinion assembly 53 with cam lid 42. Left pinion assembly 52 rotates about left longitudinal axis 60 in either a clockwise or counterclockwise direction due to its engagement with a plurality of cam lid gear teeth 54 on the inside of cam lid 42. Right pinion assembly 53 rotates about right longitudinal axis 61 in either a clockwise or counterclockwise direction due to its engagement with cam lid gear teeth 54.

Figure 13B:
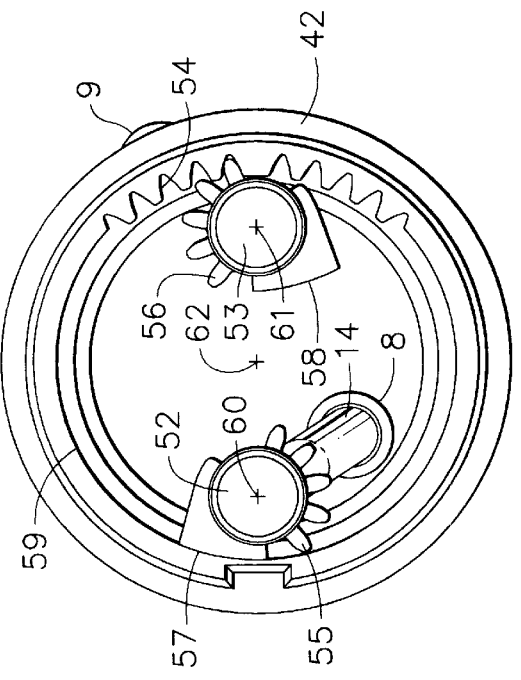
FIG. 13B is an end view of the portion of the barrel assembly illustrated in FIG. 12 for when the barrel assembly has been rotated in a counter clockwise direction about the main axis.
Figure 13C:
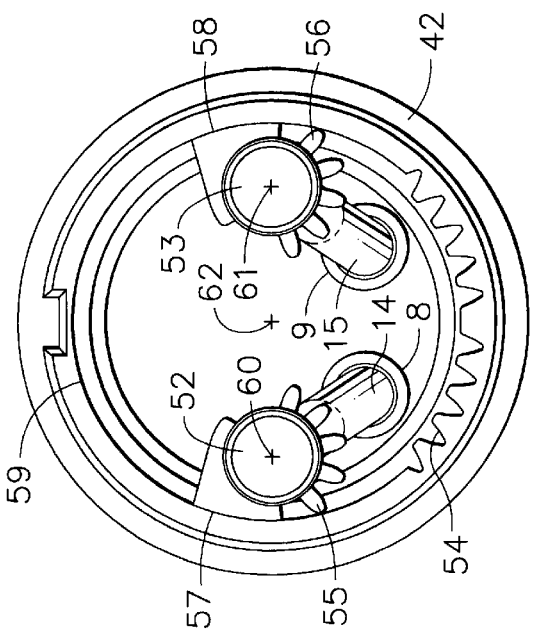
FIG. 13C is an end view of the portion of the barrel assembly illustrated in FIG. 12 for when the barrel assembly is in a centered position.
Figure 13A:
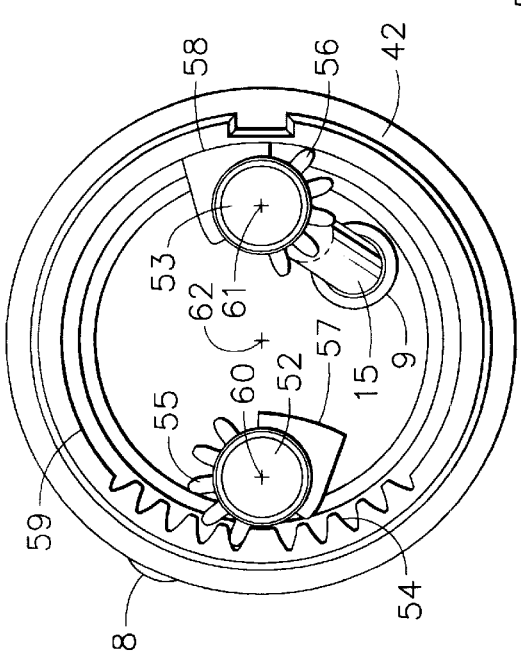
FIG. 13A is an end view of the portion of the barrel assembly illustrated in FIG. 12 for when the barrel assembly has been rotated in a clockwise direction about a main axis.

FIGS. 13A–C are end views of the components of barrel assembly 70 shown in FIG. 12, looking from the proximal to distal direction. In these views the lateral swing movement of left gripper 8 and right gripper 9 can be seen in relation to the rotational position of cam lid 42. Partial views of left gripper 8 and right gripper 9 are visible either through the open, cylindrical cam lid 42, or extending partially outside the outer perimeter of cam lid 42. In FIG. 13C, left pinion assembly 52 is shown to further comprise a plurality of left pinion gear teeth 55, and left pinion sliding surface 57. Similarly, right pinion assembly 53 is shown to further comprise a plurality of right pinion gear teeth 56, and right pinion sliding surface 58. In FIG. 13C, cam lid 42 is in middle rotational position hereinafter referred to as the "home" position. Both left pinion sliding surface 57 and right pinion sliding surface 58 are against a cam lid sliding surface 59. Cam lid gear teeth 54 are positioned midway between left pinion assembly 52 and right pinion assembly 53. Left gripper 8 and right gripper 9 are close together, as is shown in FIGS. 5A and 5E.

FIGS. 13A and 13B shown the extreme clockwise and counterclockwise positions, respectively, of cam lid 42 (and barrel assembly 70). In FIG. 13A, cam lid 42 is rotated approximately 90 degrees in the clockwise direction about main axis 62. Left pinion gear teeth 55 are engaged with cam lid gear teeth 54, resulting in the clockwise rotation of left arm 14 (not visible) and lateral swinging of left gripper 8 away from right gripper 9. FIG. 13A shows the same relative positions of left gripper 8 and right gripper 9 as is shown in FIG. 5B. In FIG. 13B, cam lid 42 is rotated approximately 90 degrees in the counterclockwise direction about main axis 62. Right pinion gear teeth 56 are engaged with cam lid gear teeth 54, resulting in the clockwise rotation of right arm 15 (not visible) and lateral swinging of right gripper 9 away from left gripper 8. FIG. 13B shows the same relative positions of left gripper 8 and right gripper 9 as is shown in FIG. 5D.

Before the rotation of the left arm 14 takes place, causing the left gripper 8 to swing away from its home position, it is necessary for the left gripper 8 to release its hold of the needle 1, while the right gripper 9 maintains its grip. (See FIG. 19.) This is also true for the when the right arm 15 swings away from its home position, that is, the right gripper 9 must first release the needle 1. The timing for the actuation of grippers 8, 9 is designed accordingly, and is controlled by the cam mechanism within the barrel 30.

FIG. 14A is a sectional view of barrel assembly 70 revealing left pinion assembly 52 and right pinion assembly 53. FIG. 14A corresponds with FIG. 13A for when barrel assembly 70 is rotated to the full clockwise position about main axis 62. Rotation of drive post 31 causes barrel cover 34 and cam lid 42 to rotate about main axis 62. Yoke 43, left pinion assembly 52, and right pinion assembly 53 remain fixed relative to main axis 62. Left arm proximal end 85 is attached to left pinion assembly 52 and right arm proximal end 84 is attached to right pinion assembly 53. Left cam head 49 is attached to left cable 40, which runs through the entire length of arm 14. Left cable 40 is attached at its distal end to left gripper head 10. Likewise, right cam head 50 is attached to right cable 41, which is attached to right gripper head 11. Left spring 46 and right spring 47 are assembled in a partially compressed configuration in order to maintain tension on left cable 40 and right cable 41, respectively. Left cables 40 and right cable 41 are flexible in order to move easily in the longitudinal direction through the offset bends, 80 and 81, of the left and right arms, 14 and 15, respectively, (see FIG. 1). Due to the constraining of left cable 40 within left arm 14, left cable 40 can push sufficiently left gripper head 10 in the distal direction in order to receive or release a needle. Likewise, right cable 41 can push right gripper head 11 in the distal direction.

Still referring to FIG. 14A, barrel cover 34 has a first peripheral cam 64 on the inside of its proximal end contacting left cam head 49 and right cam head 50. Cam lid 42 has a second peripheral cam 66 on its inside, contacting right pinion cam surface 68 and left pinion cam surface 67. In FIG. 14A, barrel assembly 70 is rotated in a full clockwise direction corresponding to FIG. 13A, causing the distance between left pinion cam surface 67 and left cam head 49 to be decreased for left pinion assembly 52, and increased for right pinion assembly 53. Left spring 46 is further compressed, so that left gripper 8 is open as shown in FIG. 5B. Second peripheral cam 66 and first peripheral cam 64 are shaped so as to cause left gripper 8 to open at least partially prior to left gripper 8 swinging laterally apart from right gripper 9. In FIG. 14A second peripheral cam 66 and first peripheral cam 64 do not further compress right spring 47. This allows right gripper 9 to maintain a holding force on needle 1.

FIG. 14B is a sectional view of barrel assembly 70 when rotated in a full counterclockwise direction, and corresponds with the positions of the left gripper 8 and right gripper 9 as shown in FIGS. 5D and 13B. In FIG. 14B, the distance between cam lid peripheral cam surface 66 and peripheral cam surface 64 is decreased for right pinion assembly 53 and increased for left pinion assembly 52. The opposite situation of FIG. 14A exists: right gripper 9 is open and left gripper 8 is closed.

Right pinion spring 47 is assembled into right pinion assembly 53 partially compressed and is shown in FIG. 14A for when it has its maximum allowable length. The longitudinal force of spring 47 causes right cam head 50 to move proximally, thereby moving cable 41 and right gripper head 9 proximally. Simultaneously, right pinion 53 has moved distally, causing right arm 15 and right arm flange 13 to move distally. These two, opposing movements provide a bi-directional grip on the needle 1. Again in FIG. 14A, left pinion spring 46 is at its minimum allowable length because left arm 14 was moved in the proximal direction and left cam head 49 was moved in the distal direction. This results in the bi-directional separation of left gripper head 10 and left arm flange 12 as can be seen in FIG. 4. This separation feature is advantageous because needle 1 is centered on the gap between gripper head 10 and arm flange 12, and therefore allowable variation of needle alignment with the gap is greater than if only gripper head 10 or arm flange 12 were to move alone. Bi-directional opening and closing is provided for both left gripper 8 and right gripper 9.

Figure 15:
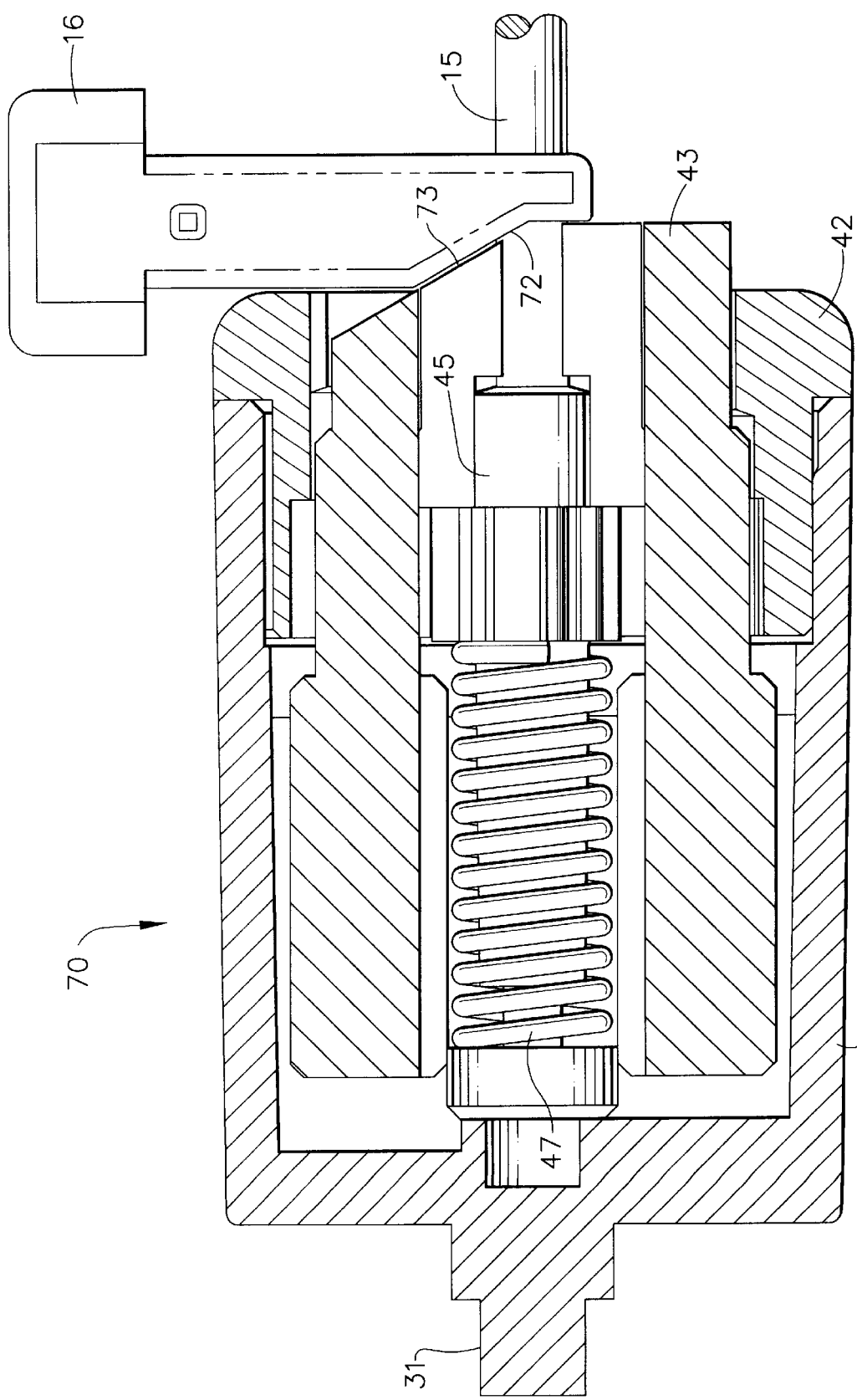
FIG. 15 is a side, sectional view of the barrel assembly and a loading button in an up position.
Figure 16:
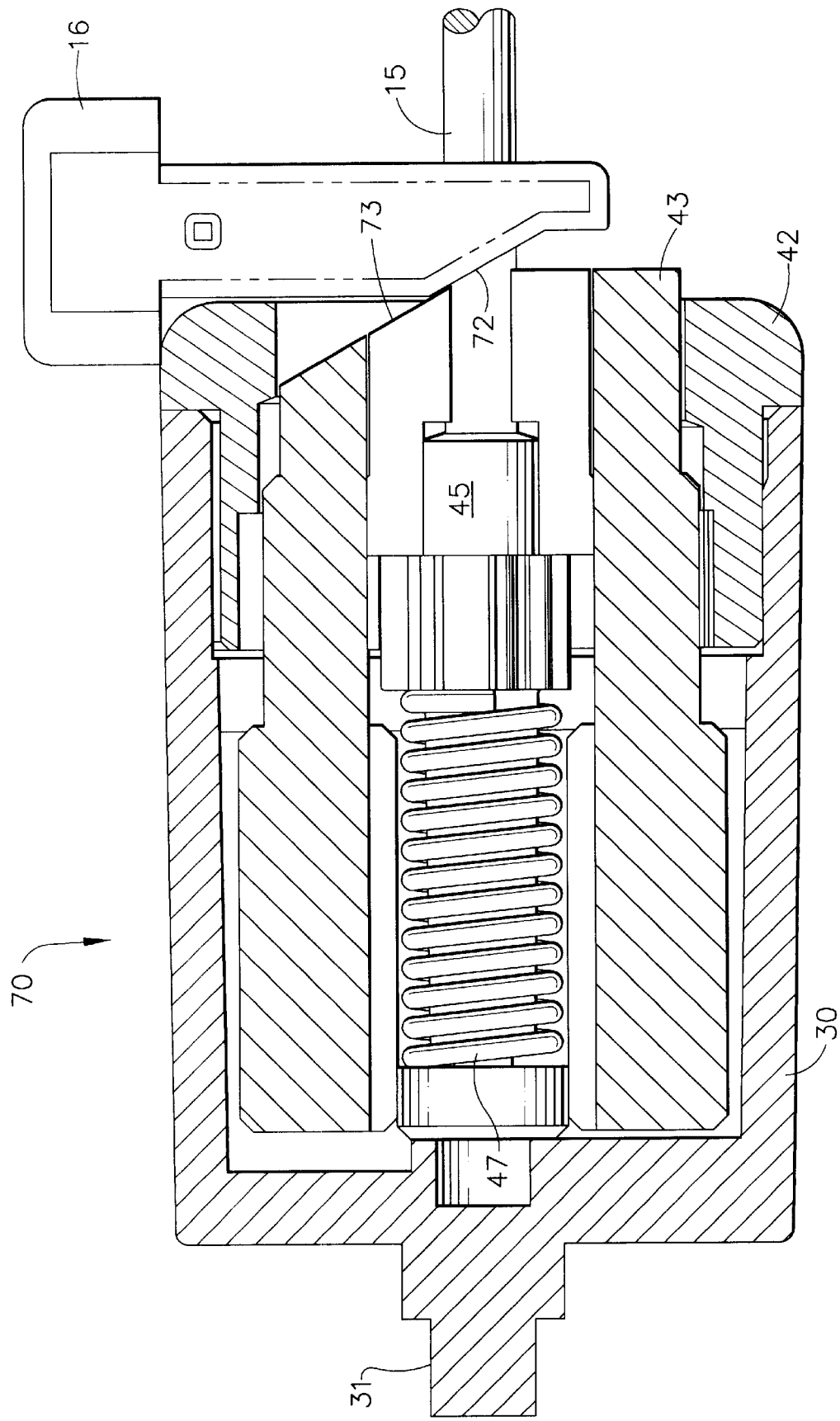
FIG. 16 is a side, sectional view of the barrel assembly and a loading button in a down position.

Now turning to FIGS. 15 and 16, the operation of button 16 for the loading and release of needle 1 from the distal end of the present invention is next described. In FIG. 5A, which corresponds to FIG. 15, needle 1 is gripped by both left gripper 8 and right gripper 9, while both are in the "home" position, and button 16 is in the full upward or non-actuated position. Button 16 is held in the upward position by the summed force exerted by left spring 46 and right springs 47, pushing against left and right cam heads, 49 and 50 respectively, and simultaneously against left pinion 44 and right pinion 45. This arrangement results in an axial force exerted on yoke 43 in the distal direction. A yoke ramp surface 73 transmits this force to a button ramp surface 72, forcing button 16 vertically upwards. FIG. 16 shows button 16 pushed downwards (by the surgeon) to push yoke 43 in the proximal direction. Yoke 43 then pushes against left pinion 44 and right pinion 45 so that left pinion spring 46 and right pinion spring 47 are further compressed, resulting in the movement in the proximal direction of left arm 14 and right arm 15. Thus, left gripper 8 and right gripper 9 open so that a needle may be placed into them. Release of Button 16 allows left gripper 8 and right gripper 9 to close onto the needle. Button ramp surface 72 abuts yoke ramp surface 73 at all times and prevents yoke 43 from rotating when barrel assembly 70 is rotated.

Figure 17:
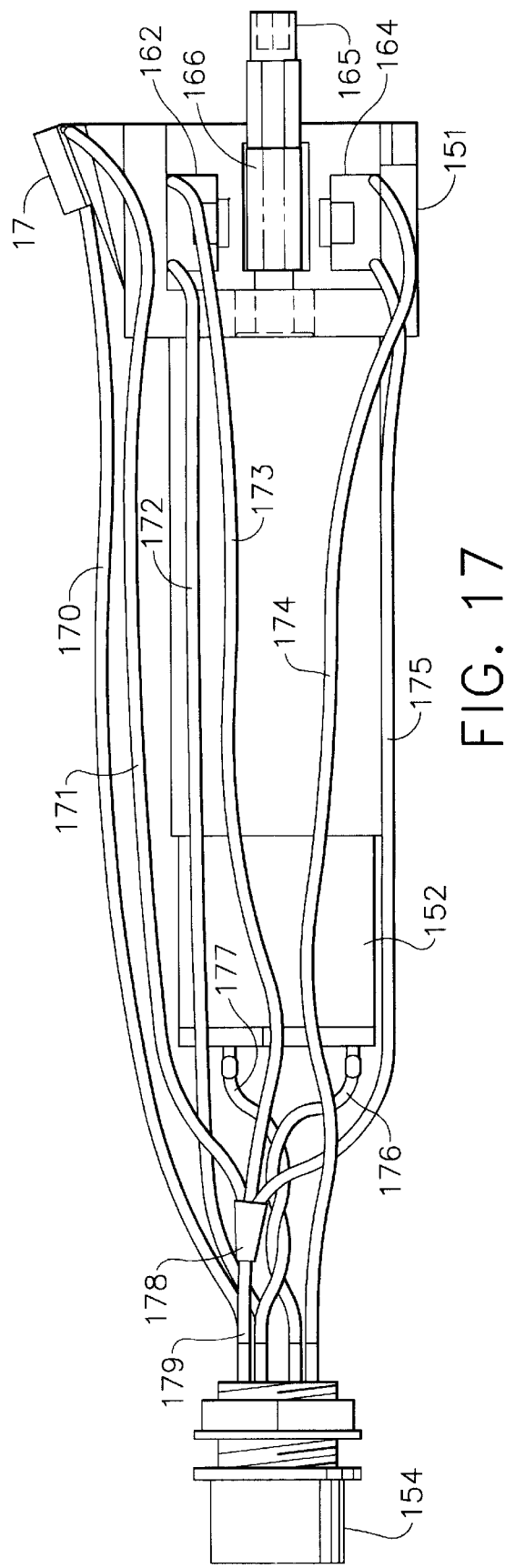
FIG. 17 is a top view of the d rive assembly illustrate d in FIG. 1; an d
Figure 18:
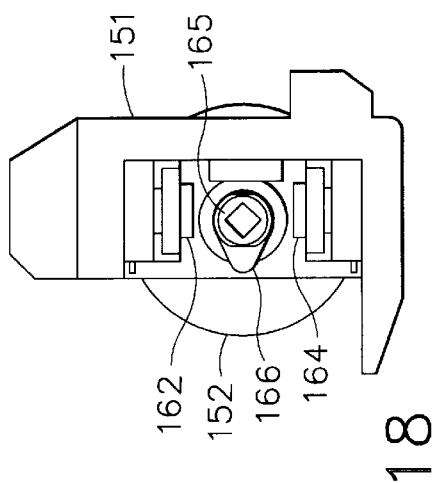
FIG. 18 is an end view of the drive assembly illustrated in FIGS. 1 and 17.

FIG. 17 is a side view of drive assembly 150 with switching cam 166 positioned midway between CCW limit switch 162 and CW limit switch 164, corresponding to FIGS. 5A, 5C, or 5E when left gripper 8 and right gripper 9 are in the "home" position. FIG. 18 is an end view of drive assembly 150, again showing switching cam 166 in the midway or "home" position. A suitable example of motor 152 is available from MicroMo Electronics, Inc. (Faulhaber Group) in Clearwater, Fla., as DC MicroMotors Series 1319, part number 1319T012S14/1,14:1 having the following specifications: 12 volts DC nominal, 14:1 planetary gearhead, no load motor speed of 17,100 rev/min, no load current of 15 mA, stall torque of 0.490 oz-in, 1.64 Watts max power output. A suitable example for switch 17, CW limit switch 162, and CCW limit switch 164 is available from Newark Electronics, Cincinnati, Ohio as part number Farnell 176-986. Panel plug 154 and cable socket 156 are available also from Newark Electronics as part numbers 147-034 and 147-028.

In FIG. 17, motor 152, switch 17, CW limit switch 164, and CCW switch 162 are each electrically connected to panel plug 154 by a pair of insulated wires as follows: a first wire 170 and a second wire 171 connect switch 17; a third wire 172 and a fourth wire 173 connect to CCW limit switch 162; a fifth wire 174 and a sixth wire 175 connect CW limit switch 164; a seventh wire 176 and an eighth wire 177 connect motor 152. Second wire 171, fourth wire 173, sixth wire 175 connect to a common connector 178 which is connected to panel plug 154 by a common wire 179.

Control unit 160 (see FIG. 1) controls motor 152 when the surgeon actuates switch 17. Control unit 160 comprises a 24 VDC (volts direct current) power supply 184, a voltage divider 182 for dividing the supplied voltage into +/−12 VDC, and a PLC (programmable logic controller) 180. A suitable example for PLC 180 is commercially available from Aromat Products, Inc. in New Providence, New Jersey as part number FPO-C10RS. PLC 180 is configured to perform the operational sequence described for FIGS. 5A–E as follows. After needle 1 is loaded in left gripper 8 and right gripper 9 as shown in FIG. 5A (by using button 16 as described for FIG. 16) the surgeon pushes and holds switch 17. Control unit 160 supplies motor 152 with +12 VDC so that it rotates CW. Left gripper 8 opens and then swings laterally away from gripper 9 as shown in FIG. 5B. Once left gripper 8 is in this position, CW limit switch 162 is actuated so that motor 152 stops, even if the surgeon is still pressing switch 17. The surgeon then releases switch 17 and may pass needle 1 through tissue. When the surgeon presses switch 17 again, control unit 160 supplies motor 152 with −12 VDC so that motor 152 rotates CCW and left gripper 8 swings laterally near gripper 9 and then closes onto needle 1. While the surgeon is still pressing switch 17, right gripper 9 releases needle 1 and swings laterally away from left gripper 8. When right gripper 8 has reached the position shown in FIG. 5D, the CCW limit switch is actuated and motor 152 stops. The surgeon may then pull needle 1 through the tissue. When the surgeon presses and holds switch 17 again, control unit 160 sends +12 VDC to motor 152 so that it rotates CW. Right gripper 9 swings laterally near left gripper 8 and closes onto needle 1 as shown in FIG. 5E.

In the foregoing discussion, the point of needle 1 was directed to the surgeon's left. The present invention may also be used when the point of needle 1 is directed to the surgeon's right. In that situation, needle 1 is loaded (by pushing button 16 as described for FIG. 16) when left gripper 8 and right gripper 9 are in the part of the operational sequence shown in FIG. 5C. The surgeon can easily ascertain what part of the operational sequence he or she is in by pressing switch 17 and observing the motions of the left and right grippers, 8 and 9, before loading needle 1.

PLC 180 of control unit 160 contains what is referred to in the art as a type of "ladder" circuit having a plurality of electrical latching/unlatching relays. Motor controllers such as PLC 180 are widely used for controlling electric motors such as motor 152 of the present invention. Other devices and methods, however, are available in the art for controlling motor 152. For example, a load sensing circuit may be incorporated into control unit 160 so that CW limit switch 164 and CCW limit switch 162 may be replaced with simple hard stops. When switching cam 166 hits against a hard stop, the current supplied to motor 152 would immediately rise, and control unit 160 would stop motor 152.

Although particular embodiments of the present invention have been shown and described, other embodiments will become apparent to those skilled in the art without departing from the spirit and scope of the present invention. The terms used in describing the invention are used in their descriptive sense and not as terms of limitations.

What is claimed is:

1. A device for use with a needle and a suture attached thereto, said device for suturing bodily tissue and comprising:
   a. a handle;
   b. a right arm extending distally from said handle, the distal end of said right arm having a right gripper attached thereto for gripping and releasing the needle;
   c. a left arm extending distally from said handle, the distal end of said left arm having a left gripper attached thereto for gripping and releasing the needle;
   d. electrically powered means for moving the distal ends of said right and left arms closely adjacent to one another and for passing a needle from one gripper to the other and thereafter for moving the distal ends of said right and left arms further apart from one another without any substantial movement of the needle with respect to said handle;
   e. a control unit for controlling said electrically powered means;
   f. a single switch on said handle for actuating said electrically powered means so as to move both said distal ends of said arms, and a button on said handle which is connected to a means for opening and closing said left and right grippers so as to insert and remove a needle to and from said left and right grippers, whereby both said switch and said button can be operated by a single hand which is holding said handle.

2. The device according to claim 1, wherein said electrically powered means comprises a drive assembly contained in said handle, said drive assembly having an electrically powered motor.

3. The device according to claim 1, wherein said control unit is detachably connected to said electrically powered means.

4. The device according to claim 1 wherein said control unit comprises a programmable logic controller for controlling the electrical power for said electrically powered means.

5. The device according to claim 1 wherein said control unit comprises a load sensing circuit for controlling the electrical power for said electrically powered means.

6. The device according to claim 1 wherein said right gripper has a first and a second right opposing member, and each of said first and said second right opposing members moves towards the other to grip the needle, and moves away from the other to release the needle, and wherein said left gripper has a first and a second left opposing member, and each of said first and said second left opposing members moves towards the other to grip the needle, and moves away from the other to release the needle.

* * * * *